(12) United States Patent
Snowden et al.

(10) Patent No.: US 7,931,944 B2
(45) Date of Patent: Apr. 26, 2011

(54) METHOD OF TREATING SUBSTRATES WITH IONIC FLUOROPOLYMERS

(75) Inventors: Hue Scott Snowden, Woodstock, GA (US); Michael D. Powers, Canton, GA (US); Phillip Andrew Schorr, Atlanta, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 10/723,146

(22) Filed: Nov. 25, 2003

(65) Prior Publication Data

US 2005/0112969 A1 May 26, 2005

(51) Int. Cl.
 *B05D 5/00* (2006.01)
 *B05D 1/36* (2006.01)
 *B32B 5/26* (2006.01)
 *B32B 5/28* (2006.01)

(52) U.S. Cl. ............... 427/412; 427/2.31; 427/393.1

(58) Field of Classification Search .......... 427/412, 427/2.1, 2.3, 2.31, 393.1, 393.4
See application file for complete search history.

(56) References Cited

U.S. PATENT DOCUMENTS

| | | | |
|---|---|---|---|
| 2,841,587 A | 7/1958 | Blanton et al. | |
| 3,061,473 A | 10/1962 | Tesoro | |
| 3,338,992 A | 8/1967 | Kinney | |
| 3,341,394 A | 9/1967 | Kinney | |
| 3,502,763 A | 3/1970 | Hartmann | |
| 3,542,615 A | 11/1970 | Dobo et al. | |
| 3,692,618 A | 9/1972 | Dorschner et al. | |
| 3,802,817 A | 4/1974 | Matsuki et al. | |
| 3,849,241 A | 11/1974 | Butin et al. | |
| 3,855,046 A | 12/1974 | Hansen et al. | |
| 4,000,233 A * | 12/1976 | Gilbert | 264/532 |
| 4,041,203 A | 8/1977 | Brock et al. | |
| 4,082,887 A * | 4/1978 | Coates | 442/114 |
| 4,115,605 A | 9/1978 | Hultman et al. | |
| 4,169,062 A * | 9/1979 | Weipert | 428/394 |
| 4,340,563 A | 7/1982 | Appel et al. | |
| 4,365,049 A | 12/1982 | Tsunoda et al. | |
| 4,382,990 A | 5/1983 | Coates | |
| 4,411,928 A * | 10/1983 | Baldwin | 427/2.3 |
| 4,426,476 A | 1/1984 | Chang | |
| 4,467,013 A | 8/1984 | Baldwin | |
| 4,547,558 A | 10/1985 | Iwatsuki | |
| 4,566,981 A | 1/1986 | Howells | |
| 4,606,737 A | 8/1986 | Stern | |
| 4,668,726 A | 5/1987 | Howells | |
| 4,721,511 A | 1/1988 | Kupits | |
| 4,795,668 A | 1/1989 | Krueger et al. | |
| 4,806,410 A | 2/1989 | Armington et al. | |
| 4,818,597 A | 4/1989 | DaPonte et al. | |
| 4,976,741 A | 12/1990 | Hisamoto et al. | |
| 5,023,130 A | 6/1991 | Simpson et al. | |
| 5,041,304 A | 8/1991 | Kusano et al. | |
| 5,045,133 A | 9/1991 | DaPonte et al. | |
| 5,057,368 A | 10/1991 | Largman et al. | |
| 5,069,970 A | 12/1991 | Largman et al. | |
| 5,084,306 A | 1/1992 | McLellan et al. | |
| 5,108,820 A | 4/1992 | Kaneko et al. | |
| 5,132,028 A | 7/1992 | Nagase et al. | |
| 5,145,727 A * | 9/1992 | Potts et al. | 428/198 |
| 5,149,576 A | 9/1992 | Potts et al. | |
| 5,151,321 A | 9/1992 | Reeves et al. | |
| 5,156,780 A | 10/1992 | Kenigsberg et al. | |
| 5,169,706 A | 12/1992 | Collier, IV et al. | |
| 5,178,931 A | 1/1993 | Perkins et al. | |
| 5,178,932 A | 1/1993 | Perkins et al. | |
| 5,188,885 A | 2/1993 | Timmons et al. | |
| 5,194,541 A | 3/1993 | Legros et al. | |
| 5,229,465 A | 7/1993 | Tsuchida et al. | |
| 5,277,976 A | 1/1994 | Hogle et al. | |
| 5,296,282 A | 3/1994 | Evers | |
| 5,336,552 A | 8/1994 | Strack et al. | |
| 5,349,003 A | 9/1994 | Kato et al. | |
| 5,382,400 A | 1/1995 | Pike et al. | |
| 5,411,576 A | 5/1995 | Jones et al. | |
| 5,436,399 A | 7/1995 | Koyama et al. | |
| 5,466,410 A | 11/1995 | Hills | |
| 5,508,343 A | 4/1996 | Holley | |
| 5,520,962 A | 5/1996 | Jones, Jr. | |
| 5,540,992 A | 7/1996 | Marcher et al. | |
| 5,589,258 A | 12/1996 | Maddern et al. | |
| 5,630,846 A | 5/1997 | Hara et al. | |
| 5,711,994 A | 1/1998 | Powers | |

(Continued)

FOREIGN PATENT DOCUMENTS

EP 0160402 B1 7/1991

(Continued)

OTHER PUBLICATIONS

INDA Standard Test, IST 80.9-74 (R-82), "Alcohol Repellency of Nonwovens", 1974 (R1982), 3 pages.

(Continued)

*Primary Examiner* — William Phillip Fletcher, III
(74) *Attorney, Agent, or Firm* — Christos S. Kyriakou; Robert A. Ambrose; Richard M. Shane (57) ABSTRACT

The present invention provides a method of treating a substrate to improve the alcohol repellency of the substrate while minimizing the effect on the hydrostatic head value of the substrate that includes contacting a substrate with a treatment solution that includes an ionic fluoropolymer, a monovalent salt, and essentially no antistatic agent or less than 0.05 weight percent by weight of an antistatic agent.

17 Claims, 4 Drawing Sheets

U.S. PATENT DOCUMENTS

| | | | |
|---|---|---|---|
| 5,804,625 | A | 9/1998 | Temperante et al. |
| 5,851,595 | A | 12/1998 | Jones, Jr. |
| 5,885,909 | A | 3/1999 | Rudisill et al. |
| 6,028,132 | A | 2/2000 | Hayashi |
| 6,114,419 | A | 9/2000 | Liss et al. |
| 6,127,485 | A | 10/2000 | Klun et al. |
| 6,197,378 | B1 | 3/2001 | Clark et al. |
| 6,225,403 | B1 | 5/2001 | Knowlton |
| 6,274,060 | B1 | 8/2001 | Sakashita et al. |
| 6,297,304 | B1 | 10/2001 | Raiford et al. |
| 6,350,399 | B1 | 2/2002 | Cook et al. |
| 6,562,428 | B1 | 5/2003 | Ohrui |
| 6,752,840 | B1 | 6/2004 | Onishi et al. |
| 6,787,184 | B2 | 9/2004 | Snowden et al. |
| 2002/0025749 | A1 | 2/2002 | Shimizu et al. |
| 2004/0124565 | A1 | 7/2004 | Schiffer et al. |

FOREIGN PATENT DOCUMENTS

| | | |
|---|---|---|
| EP | 0196759 B1 | 8/1992 |
| EP | 0737773 A1 | 10/1996 |
| EP | 0985741 A1 | 3/2000 |
| EP | 1039018 A1 | 9/2000 |
| EP | 0815306 B1 | 7/2002 |
| EP | 0624680 B1 | 10/2002 |
| GB | 1346098 | 2/1974 |
| WO | WO 94/24179 | 10/1994 |
| WO | WO 97/08243 | 6/1997 |
| WO | WO 00/52709 | 9/2000 |
| WO | WO 01/46507 | 6/2001 |
| WO | WO 01/49925 | 7/2001 |
| WO | WO 02/083406 | 10/2002 |
| WO | WO 02/103107 | 12/2002 |
| WO | WO 03/041458 | 5/2003 |

OTHER PUBLICATIONS

INDA Standard Test, IST 40.2-92, "Electrostatic Decay", 1992, pp. 77-82.

Method 5514, Federal Test Method Standard No. 191A, "Water Resistance of Cloth; Low Range, Hydrostatic Pressure Method", Jul. 1978.

Method 5450, Federal Test Method Standard No. 191A, "Permeability to Air; Cloth; Calibrated Orifice Method", Jul. 1978.

ASTM Designation: D 737-96, "Standard Test Method for Air Permeability of Textile Fabrics", Published Apr. 1996, pp. 207-211.

Abstract, JP 2002-302871 A2, Oct. 18, 2002.

Abstract, JP 02656807 B2, Sep. 24, 1997.

Abstract, JP 02981535 B2, Nov. 22, 1999.

Abstract, JP 03270930 B2, Apr. 2, 2002.

Database WPI, Derwent Publications Ltd., JP 9143882A, Jun. 3, 1997.

Patent Abstracts of Japan, JP 08284067A, Oct. 29, 1996.

* cited by examiner

METHOD OF TREATING SUBSTRATES WITH IONIC FLUOROPOLYMERS

TECHNICAL FIELD

This invention relates to nonwoven fabrics and to methods of treating nonwoven fabrics.

BACKGROUND OF THE INVENTION

The manufacture of nonwoven fabrics for diverse applications has become a highly developed technology. Methods of manufacturing nonwoven fabrics include spunbonding, meltblowing, carding, airlaying, and so forth. It is not always possible, however, to produce by these methods a nonwoven fabric having all desired attributes for a given application. As a result, it is often necessary to treat nonwoven fabrics by various means to impart desired properties. For example, for medical applications such as surgeon's gowns, barrier properties to alcohol and blood penetration and bacteria are desired, and antistatic properties are important as well. Unfortunately, treatments for barrier properties using fluorocarbons, for example, and treatments for antistatic properties using salts are detrimental to each other which make it necessary to apply excessive amounts of one or both of the treatments. Current methods of treating nonwoven fabrics require slightly to moderately charged, either cationic or anionic, fluoropolymers suspended in water and then combined with anionic antistatic agents in a single bath treatment to produce an alcohol repellent, antistatic surgical fabric. Unfortunately, the antistatic agents currently being used are surface active in nature and negatively impact the water repellency of the finished web as measured by hydrostatic head testing. In addition, antistatic agents tend to destabilize suspensions of fluoropolymers of opposing ionic charge, leading to coagulation and filter plugging issues. Efforts to completely remove the antistat from the bath and apply it downstream on the body side of the web have resulted in a loss of alcohol repellency at equivalent fluoropolymer bath concentrations due to low adsorbed amounts of fluoropolymer on the fabric.

Accordingly, there is a need for a method of topically treating surgical fabric with an alcohol repellent chemistry that does not negatively effect, or at least minimizes the effect, on the water barrier of the fabric.

SUMMARY OF THE INVENTION

The present invention provides a method of topically treating surgical fabric with an alcohol repellent chemistry that minimizes the effect on the water barrier of the fabric. In one embodiment, the method of the present invention includes contacting a substrate with a treatment solution comprising an ionic fluoropolymer and a monovalent salt wherein the treatment solution contains less than about 0.05 weight percent by weight of an antistatic agent. The substrate can be or include a nonwoven web, a foam, a film, or a porous films nonwoven fabric. More specifically, the substrate can be or include a nonwoven fabric laminate, such as a spunbond/meltblown (SM) laminate, a spunbond/meltblown/spunbond (SMS) laminate, a spunbond/film/spunbond (SFS) laminate, a spunbond/film/spunbond/meltblown/spunbond (SFSMS) laminate or a spunbond/film/film/spunbond (SFFS) laminate. Treated fabric laminates of the present invention are useful as surgical fabrics.

In certain embodiments, the treatment solution comprises less than about 0.05 weight percent of an antistatic agent or more desirably less than about 0.005 weight percent by weight of an antistatic agent. Most desirably, the treatment solution includes no antistatic agent and the method further comprises contacting the substrate with a second solution that may include an antistatic agent. For example, in certain embodiments, the method includes contacting one side of the treated substrate with a second treatment that includes an antistatic agent. The antistatic agent may be an organic phosphate ester, for example ZELEC® organic phosphate ester antistatic agent or a QUADRASTAT® antistatic agent. In certain embodiments, the treatment solution comprises less than about 0.20 weight percent of a monovalent salt or a mixture of monovalent salts. In certain embodiments, the treatment solution includes less than about 0.10 weight percent of a monovalent salt or a mixture of monovalent salts. In certain embodiments, the treatment solution includes less than about 0.05 weight percent of a monovalent salt or a mixture of monovalent salts. In certain embodiments, the treatment solution includes less than about 2.0 weight percent of an ionic fluoropolymer or a mixture of ionic fluoropolymers, more desirably, less than about 1.0 weight percent of an ionic fluoropolymer or a mixture of ionic fluoropolymers, most desirably, between about 0.1 and about 1 weight percent of an ionic fluoropolymer or a mixture of ionic fluoropolymers. The method may further include drying the treated substrate wherein the dried substrate includes less than about 0.5 weight percent fluorine, more desirably, less than about 0.25 weight percent fluorine, and even more desirably, less than about 0.15 weight percent fluorine as determined through elemental analysis based on the weight of treated fabric. The treatment solution may be an aqueous treatment solution and may further include an alcohol, for example an alkyl alcohol such as octanol. In certain desirable embodiments, the treatment solution includes less than about 0.2 weight percent of a monovalent salt or a mixture of monovalent salts where the monovalent salts including, but not limited to, sodium chloride, sodium nitrate, sodium carbonate, lithium chloride, lithium nitrate, lithium carbonate, potassium chloride, potassium nitrate, potassium carbonate and mixtures thereof. Suggested ionic fluoropolymers include, but are not limited to fluoroalkyl acrylate homopolymers, fluoroalkyl acrylate copolymers, fluorinated siloxanes, fluorinated silicones, fluorinated urethanes, and mixtures thereof. Desirably, the treatment solutions of the present invention do not require a non-ionic, permanent wetting agent such as an ethoxylated fatty alcohol or polyoxyethylene. Moreover, treatment solutions of the present invention do not require a silicon containing compound, such as a silyl quaternary amine.

In one particular embodiment, the present invention provides a method of improving the alcohol repellency of a nonwoven substrate by applying a topical treatment to a nonwoven substrate while minimizing any negative effect of the topical treatment on the water repellency of the nonwoven substrate, the method comprising: providing a nonwoven substrate; contacting the nonwoven substrate with an aqueous topical treatment solution that does not include an organic phosphate ester, wherein the treatment solution comprises water, less than about 0.20 weight percent of a monovalent salt or a mixture of monovalent salts and less than about 2.0 weight percent of an ionic fluoropolymer or a mixture of ionic fluoropolymers; wherein the monovalent salts are selected from the group consisting of sodium chloride, sodium nitrate, sodium carbonate, lithium chloride, lithium nitrate, lithium carbonate, potassium chloride, potassium nitrate, and potassium carbonate; the ionic fluoropolymers are selected from the group consisting of cationic and anionic fluoroalkyl acrylate homopolymers, fluoroalkyl acrylate copolymers, fluorinated siloxanes, fluorinated silicones, fluorinated urethanes, and mixtures thereof; and then contacting a surface of the topically treated nonwoven substrate with an antistatic agent selected from the group consisting of organic phosphate esters. Advantageously, an antistatic agent can applied to the substrate in a separate step after the ionic fluoropolymer is applied. More advantageously an antistatic agent can be applied to only one surface of the substrate in order to minimize any negative effect of the antistatic agent on the water repellency and/or alcohol repellency.

The present invention also provides improved nonwoven substrates treated by the above methods. Previous treatment chemistries that make use of surface active antistatic agents at concentrations greater than 0.05 weight percent can lower the hydrostatic head by 45 percent or more compared to the untreated fabric as measured by FTS 191A, Method 5514. This greatly diminishes the level of water barrier provided by the finished product. Thus, the present invention provides alcohol repellant-treated nonwoven fabrics having a percent loss in hydrostatic head value as compared to untreated fabric of about 30%, 25%, 15%, 10% or less as measured by Federal Test Standard 191A, Method 5514. In certain embodiments, treated nonwoven fabrics also have an alcohol repellency of at least about 60%, 70%, 75%, 80% and 90% isopropanol in water as measured by INDA Standard Test No. IST 80.9-74 (R-82). In certain embodiments, a nonwoven fabric includes a first surface and a second, opposing surface wherein the first surface comprises an ionic fluoropolymer and a monovalent salt and the second surface that comprises an antistatic agent.

In one embodiment, a laminate of the present invention includes at least one meltblown nonwoven layer wherein the nonwoven fabric laminate is treated for alcohol repellency while losing only about 30 percent of the initial hydrostatic head value. For example, an untreated base fabric had a hydrostatic head of 85 mBar and an IPA repellency of 20 percent. The present invention provides a treated fabric having an IPA repellency of at least about 90 percent while maintaining a hydrostatic head value of at least about 60 mBar, a drop in hydrostatic head of less than 30 percent. In another embodiment, the present invention provides a treated fabric laminate having an IPA repellency of at least about 60 percent while maintaining a hydrostatic head value of at least about 65 m Bar, a drop in hydrostatic head of less than 25 percent compared to the untreated fabric. In yet another embodiment, the present invention provides a treated fabric laminate having an IPA repellency of at least about 90 percent while maintaining a hydrostatic head value of at least about 65 mBar, a drop in hydrostatic head of less than 25 percent. In yet another embodiment, the present invention provides a treated fabric laminate having an IPA repellency of at least about 60 percent while maintaining a hydrostatic head value of at least about 70 mBar, a drop in hydrostatic head of less than 20 percent. In yet another embodiment, the present invention provides a treated fabric laminate having an IPA repellency of at least about 80 percent while maintaining a hydrostatic head value of at least about 70 mBar, a drop in hydrostatic head of less than 15 percent. In yet another embodiment, the present invention provides a treated fabric laminate having an IPA repellency of at least about 90 percent while maintaining a hydrostatic head value of at least about 70 m Bar, a drop in hydrostatic head of less than 15 percent. In yet another embodiment, the present invention provides a treated fabric laminate having an IPA repellency of at least about 80 percent while maintaining a hydrostatic head value of at least about 80 mBar, drop in hydrostatic head of less than 10 percent.

BRIEF DESCRIPTION OF THE DRAWINGS

The invention will be more fully understood and further advantages will become apparent when reference is made to various embodiments described in the following description and accompanying drawings in which.

Repeated use of reference characters in the present specification and drawings is intended to represent same or analogous features or elements of the present invention.

Test Procedures

Hydrostatic Head: A measure of the liquid barrier properties of a fabric is the hydrostatic head test. The hydrostatic head test determines the height of water (in centimeters) which the fabric will support before a predetermined amount of liquid passes through. A fabric with a higher hydrostatic head reading indicates it has a greater barrier to liquid penetration than a fabric with a lower hydrostatic head. The hydrostatic head test is performed according to Federal Test Standard 191A, Method 5514.

The test is modified to include a screen support of standard synthetic fiber window screen material. The test head of a Textest® FX-300 Hydrostatic Head Tester, available from Schmid Corporation, having offices in Spartanburg, S.C. was filled with purified water. The purified water was maintained at a temperature between 65° F. and 85° F. (between about 18.3° C. and 29.4° C.), which was within the range of normal ambient conditions (about 73° F. (about 23° C.) and about 50% relative humidity) at which this test was conducted. An 8 inch by 8 inch (about 20.3 cm by 20.3 cm) square sample of the test material was placed such that the test head reservoir was covered completely. The sample was subjected to a standardized water pressure, increased at a constant rate until leakage was observed on the outer surface of the sample material. Hydrostatic pressure resistance was measured at the first sign of leakage in three separate areas of the sample. This test was repeated for forty specimens of each sample material. The hydrostatic pressure resistance results for each specimen were averaged and recorded in millibars, Again, a higher value indicates greater resistance to water penetration and is desirable for barrier applications.

Alcohol: The alcohol repellency test is designed to measure the resistance of nonwoven fabrics to penetration by low surface tension liquids, such as alcohol/water solutions. Alcohol repellency was tested according to the test procedure described as follows. In this test, a fabric's resistance to penetration by low surface energy fluids is determined by placing 0.1 ml of a specified volume percentage of isopropyl alcohol (IPA) solution in several different locations on the surface of the fabric and leaving the specimen undisturbed for 5 minutes. In this test, 0.1 ml of serially diluted isopropyl alcohol and distilled water solutions, ranging from 60 volume percent to 100 volume percent increments of 10 percent, are placed on a fabric sample arranged on a flat surface. After 5 minutes, the surface is visually inspected and the highest concentration retained by the fabric sample is noted. For example, if the minimum value is a 70% IPA solution, i.e. a 70% IPA solution is retained by the fabric but an 80% solution penetrates through the fabric to the underlying surface. The grading scale ranges from 0 to 5, with 0 indicating the IPA solution wets the fabric and 5 indicating maximum repellency. Unless stated otherwise, the percent alcohol (IPA) repellency reported indicates the maximum volume percent of IPA that could be added to water while still retaining a 5 rating on the scale at all points of the fabric tested. This procedure is a modification of INDA Standard Test No. IST 80.9-74 (R-82).

Resistance to Blood Penetration (RBP): The blood strikethrough or resistance to blood penetration of a fabric is a measure of the amount of blood which penetrates the fabric at a particular pressure. The blood strikethrough is performed by weighing a blotter placed next to the fabric before and after the test which consists of applying 1 pound per square inch gauge (psig) pressure to the side of the fabric away from the blotter, which side has blood thereon. The pressure is ramped up over approximately 10 seconds and removed when it reaches 1 psig. The difference in the weight of the blotter before and after the test in grams represents the amount of blood which has penetrated the fabric.

Grab Tensile test: The grab tensile test is a measure of breaking strength and elongation or strain of a fabric when subjected to unidirectional stress. This test is known in the art and conforms to the specifications of Method 5100 of the Federal Test Methods Standard 191A. The results are expressed in pounds or grams to break and percent stretch before breakage. Higher numbers indicate a stronger, more stretchable fabric. The term "load" means the maximum load or force, expressed in units of weight, required to break or rupture the specimen in a tensile test. The term "total energy" means the total energy under a load versus elongation curve as expressed in weight-length units. The term "elongation" means the increase in length of a specimen during a tensile test. The grab tensile test uses two clamps, each having two jaws with each jaw having a facing in contact with the sample. The clamps hold the material in the same plane, usually vertically, separated by 3 inches (76 mm) and move apart at a specified rate of extension. Values for grab tensile strength and grab elongation are obtained using a sample size of 4 inches (102 mm) by 6 inches (152 mm), with a jaw facing size of 1 inch (25 mm) by 1 inch, and a constant rate of extension of 300 mm/min. The sample is wider than the clamp jaws to give results representative of effective strength of fibers in the clamped width combined with additional strength contributed by adjacent fibers in the fabric. The specimen is clamped in, for example, a Sintech 2 tester, available from the Sintech Corporation, 1001 Sheldon Drive, Cary, N.C. 27513, an Instron® Model TM, available from the Instron Corporation, 2500 Washington Street, Canton, Mass. 02021, or a Thwing-Albert Model INTELLECT II available from the Thwing-Albert Instrument Co., 10960 Dutton Road, Philadelphia, Pa. 19154. This closely simulates fabric stress conditions in actual use. Results are reported as an average of three specimens and may be performed with the specimen in the cross direction (CD) or the machine direction (MD).

Antistatic properties were measured according to INDA Standard Test 40.2-92.

Porosity results were obtained by Frazier Porosity tests, ASTM Standard D737 "Air Permeability of Textile Fabrics," also Method 5450 Federal Test Methods Standard No. 191A, except that the specimen size is 8 inches by 8 inches.

DEFINITIONS

As used herein and in the claims, the term "comprising" is inclusive or open-ended and does not exclude additional unrecited elements, compositional components, or method steps.

As used herein, the term "nonwoven fabric or web" means a web having a structure of individual fibers or threads which are interlaid, but not in an identifiable manner as in a knitted fabric. Nonwoven fabrics or webs have been formed from many processes such as for example, meltblowing processes, spunbonding processes, and bonded carded web processes. The basis weight of nonwoven fabrics is usually expressed in ounces of material per square yard (osy) or grams per square meter (gsm) and the fiber diameters useful are usually expressed in microns or an equivalent but more recognized term, micrometers. (Note that to convert from osy to gsm, multiply osy by 33.91). As used herein the term "spunbonded fibers" refers to small diameter fibers which are formed by extruding molten thermoplastic material as filaments from a plurality of fine, usually circular capillaries of a spinneret with the diameter of the extruded filaments then being rapidly reduced as by, for example, in U.S. Pat. No. 4,340,563 to Appel et al., U.S. Pat. No. 3,692,618 to Dorschner et al., U.S. Pat. No. 3,802,817 to Matsuki et al., U.S. Pat. Nos. 3,338,992 and 3,341,394 to Kinney, U.S. Pat. No. 3,502,763 to Hartman, and U.S. Pat. No. 3,542,615 to Dobo et al. Spunbond fibers are generally not tacky when they are deposited onto a collecting surface. Spunbond fibers are generally continuous and have average diameters (from a sample of at least 10) larger than 7 microns, more particularly, between about 10 and 20 microns. The fibers may also have shapes such as those described in U.S. Pat. No. 5,277,976 to Hogle et al., U.S. Pat. No. 5,466,410 to Hills and U.S. Pat. Nos. 5,069,970 and 5,057,368 to Largman et al., which describe fibers with unconventional shapes.

As used herein, the term "meltblown fibers" means fibers formed by extruding a molten thermoplastic material through a plurality of fine, usually circular, die capillaries as molten threads or filaments into converging high velocity, usually hot, gas (e.g. air) streams which attenuate the filaments of molten thermoplastic material to reduce their diameter, which may be to microfiber diameter. Thereafter, the meltblown fibers are carried by the high velocity gas stream and are deposited on a collecting surface to form a web of randomly dispersed meltblown fibers. Such a process is disclosed, for example, in U.S. Pat. No. 3,849,241 to Butin et al. Meltblown fibers are microfibers which may be continuous or discontinuous, are generally smaller than 10 microns in average diameter, and are generally tacky when deposited onto a collecting surface.

As used herein, the term "multilayer laminate" means a laminate wherein some of the layers, for example, are spunbond and some meltblown such as a spunbond/meltblown/spunbond (SMS) laminate and others as disclosed in U.S. Pat. No. 4,041,203 to Brock et al., U.S. Pat. No. 5,169,706 to Collier, et al, U.S. Pat. No. 5,145,727 to Potts et al., U.S. Pat. No. 5,178,931 to Perkins et al. and U.S. Pat. No. 5,188,885 to Timmons et al. Such a laminate may be made by sequentially depositing onto a moving forming belt first a spunbond fabric layer, then a meltblown fabric layer and last another spunbond layer and then bonding the laminate in a manner described below. Alternatively, the fabric layers may be made individually, collected in rolls, and combined in a separate bonding step. Such fabrics usually have a basis weight of from about 0.1 to 12 osy (3 to 400 gsm), or more particularly from about 0.75 to about 3 osy. Multilayer laminates may also have various numbers of meltblown layers or multiple spunbond layers in many different configurations and may include other materials like films (F) or coform materials, e.g. SMMS, SM, SFS, etc.

As used herein, the term "polymer" generally includes but is not limited to, homopolymers, copolymers, such as for example, block, graft, random and alternating copolymers, terpolymers, etc. and blends and modifications thereof. Furthermore, unless otherwise specifically limited, the term "polymer" shall include all possible geometrical configurations of the molecule. These configurations include, but are not limited to isotactic, syndiotactic and random symmetries.

As used herein, the term "conjugate fibers" refers to fibers which have been formed from at least two polymers extruded from separate extruders but spun together to form one fiber. Conjugate fibers are also sometimes referred to as multicomponent or bicomponent fibers. The polymers are usually different from each other though conjugate fibers may be monocomponent fibers. The polymers are arranged in substantially constantly positioned distinct zones across the cross-section of the conjugate fibers and extend continuously along the length of the conjugate fibers. The configuration of such a conjugate fiber may be, for example, a sheath/core arrangement wherein one polymer is surrounded by another or may be a side by side arrangement, a pie arrangement or an "islands-in-the-sea" arrangement. Conjugate fibers are taught in U.S. Pat. No. 5,108,820 to Kaneko et al., U.S. Pat. No. 4,795,668 to Krueger et al., U.S. Pat. No. 5,540,992 to Marcher et al. and U.S. Pat. No. 5,336,552 to Strack et al. Conjugate fibers are also taught in U.S. Pat. No. 5,382,400 to Pike et al. and may be used to produce crimp in the fibers by using the differential rates of expansion and contraction of the two (or more) polymers. Crimped fibers may also be produced by mechanical means and by the process of German Patent no. DT 25 13 251 A1. For two component fibers, the polymers may be present in ratios of 75/25, 50/50, 25/75 or any other desired ratios. The fibers may also have shapes such as those described in U.S. Pat. No. 5,277,976 to Hogle et al., U.S. Pat. No. 5,466,410 to Hills and U.S. Pat. Nos. 5,069,970 and 5,057,368 to Largman et al., which describe fibers with unconventional shapes.

As used herein, "thermal point bonding" involves passing a fabric or web of fibers to be bonded between a heated calender roll and an anvil roll. The calender roll is usually, though not always, patterned in some way so that the entire fabric is not bonded across its entire surface, and the anvil roll is usually flat. As a result, various patterns for calender rolls have been developed for functional as well as aesthetic reasons. One example of a pattern has points and is the Hansen Pennings or "H&P" pattern with about a 30% bond area with about 200 bonds/square inch as taught in U.S. Pat. No. 3,855,046 to Hansen and Pennings. The H&P pattern has square point or pin bonding areas wherein each pin has a side dimension of 0.038 inches (0.965 mm), a spacing of 0.070 inches (1.778 mm) between pins, and a depth of bonding of 0.023 inches (0.584 mm). The resulting pattern has a bonded area of about 29.5%. Another typical point bonding pattern is the expanded Hansen Pennings or "EHP" bond pattern Which produces a 15% bond area with a square pin having a side dimension of 0.037 inches (0.94 mm), a pin spacing of 0.097 inches (2.464 mm) and a depth of 0.039 inches (0.991 mm). Another typical point bonding pattern designated "714" has square pin bonding areas wherein each pin has a side dimension of 0.023 inches, a spacing of 0.062 inches (1.575 mm) between pins, and a depth of bonding of 0.033 inches (0.838 mm). The resulting pattern has a bonded area of about 15%. Yet another common pattern is the C-Star pattern which has a bond area of about 16.9%. The C-Star pattern has a cross-directional bar or "corduroy" design interrupted by shooting stars. Other common patterns include a diamond pattern with repeating and slightly offset diamonds with about a 16% bond area and a wire weave pattern looking as the name suggests, e.g. like a window screen, with about a 19% bond area. Typically, the percent bonding area varies from around 10% to around 30% of the area of the fabric laminate web. As is well known in the art, the spot bonding holds the laminate layers together as well as imparts integrity to each individual layer by bonding filaments and/or fibers within each layer.

As used herein, the term "infection control product" means medically oriented items such as surgical gowns and drapes, face masks, head coverings like bouffant caps, surgical caps and hoods, footwear like shoe coverings, boot covers and slippers, wound dressings, bandages, sterilization wraps, wipers, garments like lab coats, coveralls, aprons and jackets, patient bedding, stretcher and bassinet sheets, and the like.

As used herein the term "antistatic agent" refers to a reagent capable of preventing, reducing or dissipating static electrical charges that may be produced on textile materials such as nonwoven surgical gowns. Antistatic agents include ZELEC® organic phosphate esters available from Stepan Chemical and QUADRASTAT® mono- and di-substituted potassium isobutyl phosphate from Manufacturers Chemical of Cleveland, Tenn.

Composition percent amounts herein are expressed by weight unless otherwise indicated.

DETAILED DESCRIPTION OF THE INVENTION

The present invention relates to treatment of substrates to impart desired properties to substrates. Suggested substrates include, but are not limited to, nonwoven fabrics, films, particularly porous films and foams. Suggested nonwoven fabrics include laminates including at least one meltblown (M) layer and/or at least one spunbond layer (S), spunbond/meltblown (SM) laminates, spunbond/meltblown/spunbond (SMS) laminates, spunbond/film/spunbond (SFS) laminates, spunbond/film/spunbond/meltblown/spunbond (SFSMS) laminates and spunbond/film/film/spunbond (SFFS) laminate and laminates and combinations thereof. The invention also relates to resulting nonwoven fabrics having, for example, one surface that is alcohol repellent and the other that has antistatic properties suitable for use in the manufacture of infection control medical products including surgical gowns and sterilization wrap. Such nonwoven fabrics also have excellent barrier properties as measured by hydrostatic head and are useful as surgical fabrics and as components in surgical gowns, drapes, surgical packs and so forth. Advantageously, fabrics and fabric laminates of the present invention can be made at lower basis weights while maintaining acceptable barrier properties.

The present invention is described by reference to the test methods and definitions described above and to specific embodiments of the invention, one or more examples of which are set forth below. Each example is provided by way of explanation of the invention, not as a limitation of the invention. In fact, it will be apparent to those skilled in the art that various modifications and variations can be made in this invention without departing from the scope or spirit of the invention. For instance, features illustrated or described as part of one embodiment can be used on another embodiment to yield a still further embodiment. Thus, it is intended that the present invention cover such modifications and variations as come within the scope of the appended claims and their equivalents. Other objects, features and aspects of the present invention are disclosed in or are obvious from the following detailed description. It is to be understood by one of ordinary skill in the art that the present discussion is a description of exemplary embodiments only, and is not intended as limiting the broader aspects of the present invention, which broader aspects are embodied in the exemplary constructions.

The present invention provides an improved method of topically treating nonwoven fabrics with a repellent chemistry that improves alcohol repellency of the fabric while minimizing any negative effect on the water barrier of the fabric. In one exemplary embodiment, the method of treating nonwoven fabrics includes treating a nonwoven fabric with a solution or a suspension that includes an ionic fluoropolymer, a monovalent salt and no antistatic agent or essentially no antistatic agent. It is believed that inclusion of antistatic agents negatively affect the water repellency of the fabric. Desirably, the amount of antistatic agent in the treatment solution is less than 0.05 weight percent, more desirably, less than 0.005 weight percent and most desirably the treatment solution includes no or essentially no antistatic agent. Antistatic agents have been observed to destabilize ionic fluoropolymer suspensions in the treatment bath solution or suspension. Destabilization of the treatment bath is undesirable and causes coagulation and filter plugging during the treatment process. Ionic fluoropolymers include both cationically and anionically charged fluoropolymers and solutions and suspensions of such fluoropolymers. One suggested ionic fluoropolymer was obtained under the trade designation UNIDYNE® TG-KC01. UNIDYNE® TG-KC01 is a cationic fluoropolymer suspension that was supplied by Daikin America, Inc. of Orangeberg, N.Y. an affiliate of Daikin Industries, Ltd of Japan. Other suggested ionic fluoropolymers include, but are not limited to, commercially available charged fluoropolymer solutions that can be obtained from Daikin America, Inc. such as UNIDYNE® TG-470, UNIDYNE® TG-571 and UNIDYNE® TG-573. These fluoropolymer solutions are marketed as fabric and carpet protectants. UNIDYNE® TG-470 is an emulsion of about 30 weight percent of a weakly cationic fluoroalkyl acrylate copolymer, about 62 weight percent water and 8 weight percent of tripropylene glycol. Yet another commercially available charged fluoropolymer solution includes, but are not limited to, REPEARL® F-23 fluorochemical finish from Mitsubishi International Corporation of New York. REPEARL® F-23 fluorochemical finish is characterized as a weakly cationic fluoropolymer and is a 30 weight percent emulsion of a fluoroacrylate copolymer in 20 weight percent dipropylene glycol and 50 weight percent water. Suggested ionic fluoropolymer concentrations in the fluoropolymer treatment bath include less than about 2.0 weight percent, less than about 1.0 percent and desirably from about 0.1 to about 1.0 weight percent ionic fluoropolymer or a combination of ionic fluoropolymers.

Monovalent salts are well known and include, but are not limited to, the following inorganic monovalent salts: sodium chloride, sodium nitrate, sodium carbonate, lithium chloride, lithium nitrate, lithium carbonate, potassium chloride, potassium nitrate, potassium carbonate and so forth. Suggested monovalent salts, include but are not limited to, sodium nitrate and potassium nitrate. Suggested concentrations of monovalent salt in the treatment solution or emulsion include less than 0.2 weight percent monovalent salt or mixture of monovalent salts, more desirably less than about 0.10 weight percent of monovalent salt or mixture of monovalent salts, and most desirably less than about 0.05 weight percent of a monovalent salt or a mixture of monovalent salts.

Antistatic agents are reagents that prevent or greatly reduce electrical charges that may be produced on textile materials and are also referred to as antistats. Antistatic agents include organic phosphate esters such as ZELEC® KC, an alkyl phosphate ester from Stepan Chemical that may include mono- and disubstituted potassium n-butyl phosphate and QUADRASTAT® PIBK, mono- and di-substituted potassium isobutyl phosphate from Manufacturers Chemical of Cleveland, Tenn.

Figure 1:
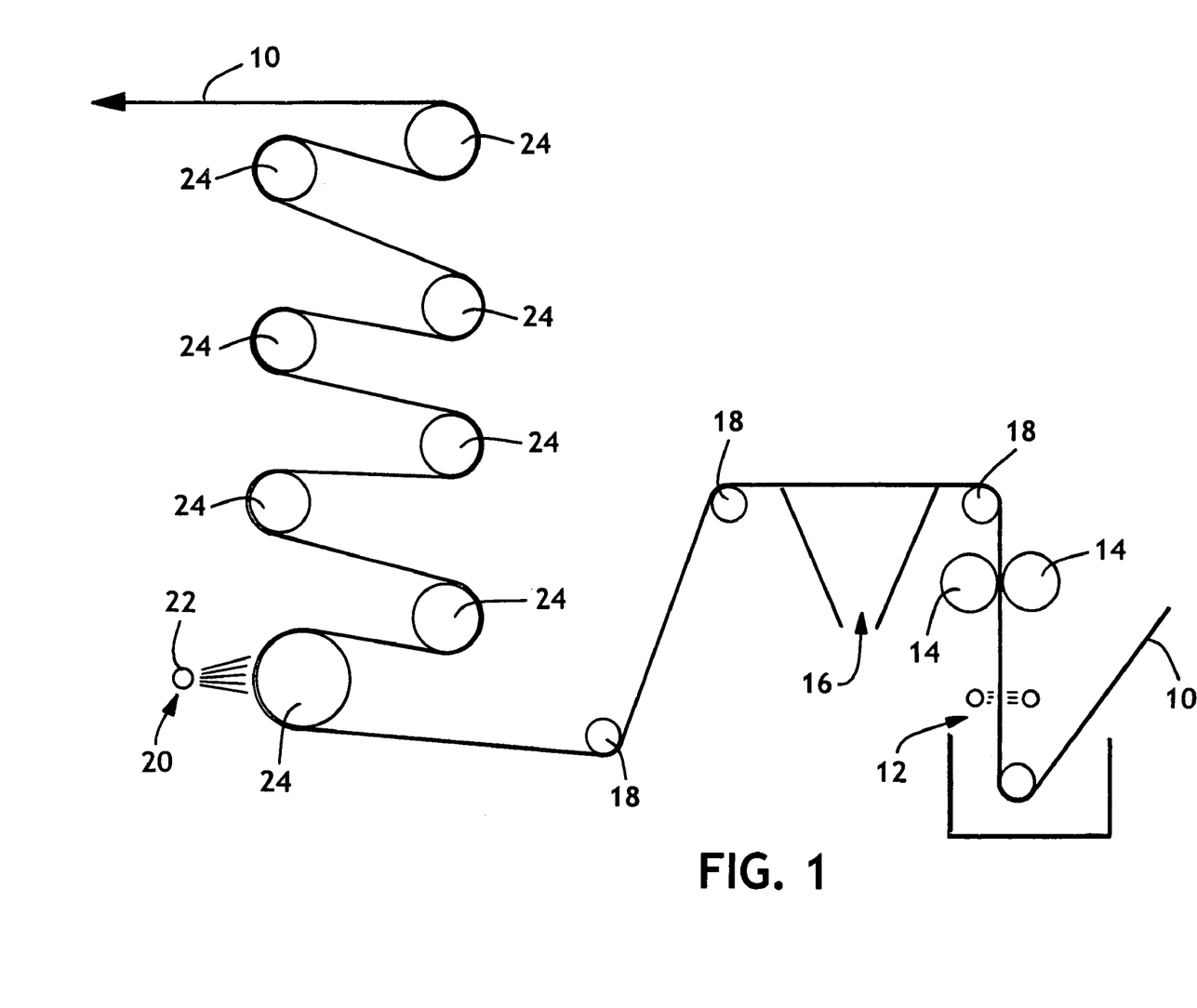
FIG. 1 is a schematic of one treatment process embodiment of the present invention using a saturation treatment step followed by a spray treatment step.

Turning to the drawings, FIG. 1 shows a web 10, for example a nonwoven fabric web, traveling from right to left. At saturation spray device 12, a fluorocarbon spray is applied to both sides. Squeeze nip rolls 14 remove excess fluorocarbon and vacuum extractor 16 removes additional treatment composition as web 10 travels over guide rolls 18. At treatment station 20 an antistat is applied to one side only of web 10 by spray device 22 and at a point preferably prior to full curing of the fluorocarbon. Web 10 is then dried by contact with steam cans 24. It is suggested that only one side, the body side, of a nonwoven fabric that is to be used as a surgical gown or other barrier is treated with an antistat so that the antistat does not interfere with the water repellency of the exterior side of the fabric.

Figure 2:
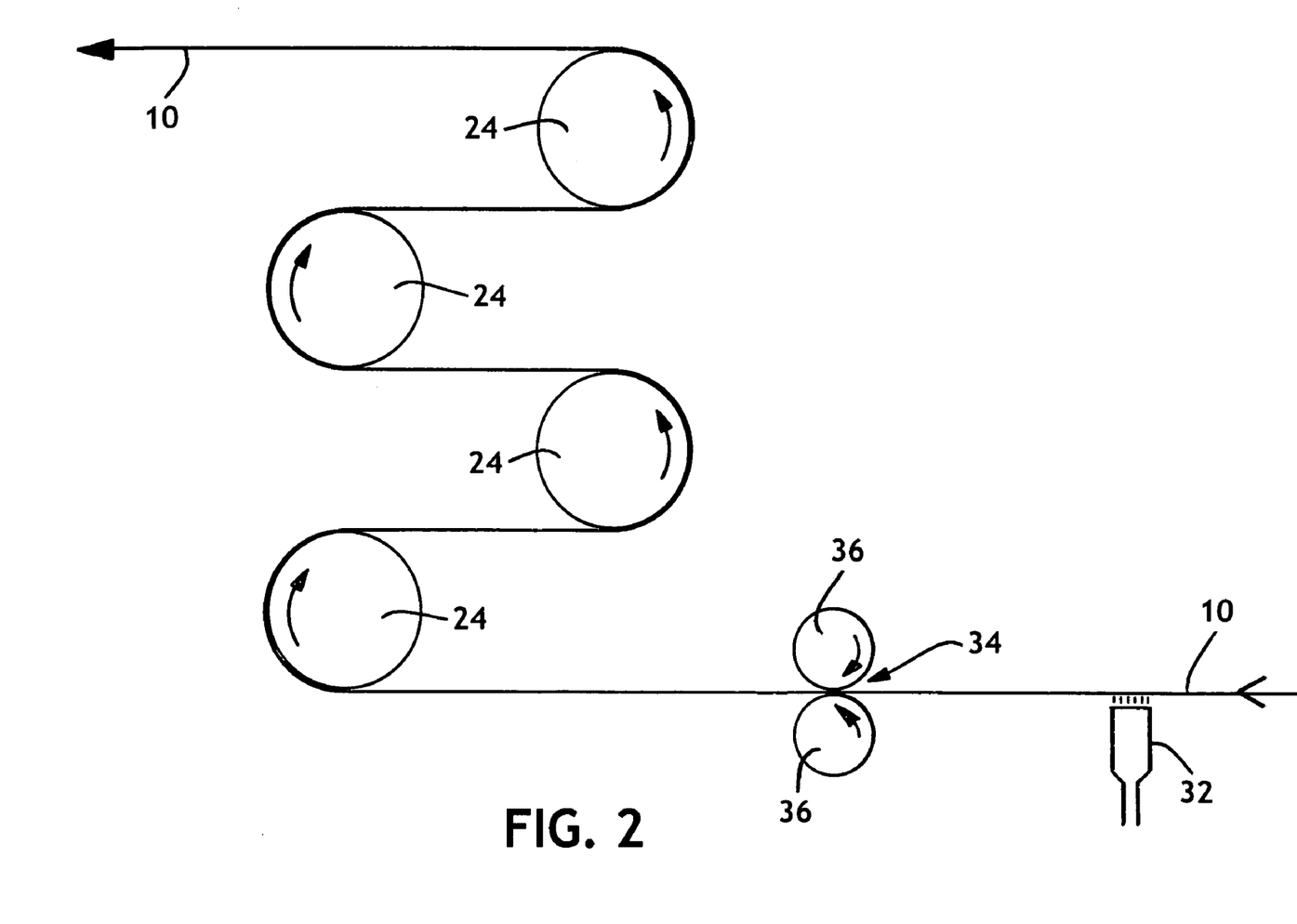
FIG. 2 is a schematic of a second treatment process embodiment of the present invention using a foam applicator instead of a spray treatment step.

FIG. 2 shows a process using a foam applicator to apply the fluorochemical instead of an antistatic spray device 22 as in FIG. 1. For FIG. 2, the system may be the same as FIG. 1 prior to the antistat spray 20 (FIG. 1) and is not shown. In FIG. 2, foam applicator 32 applies fluorocarbon composition as a foam. Excess is removed in the nip 34 between squeeze rolls 36, and web 10 is directed over steam cans 24 for drying as in FIG. 1.

Figure 3:
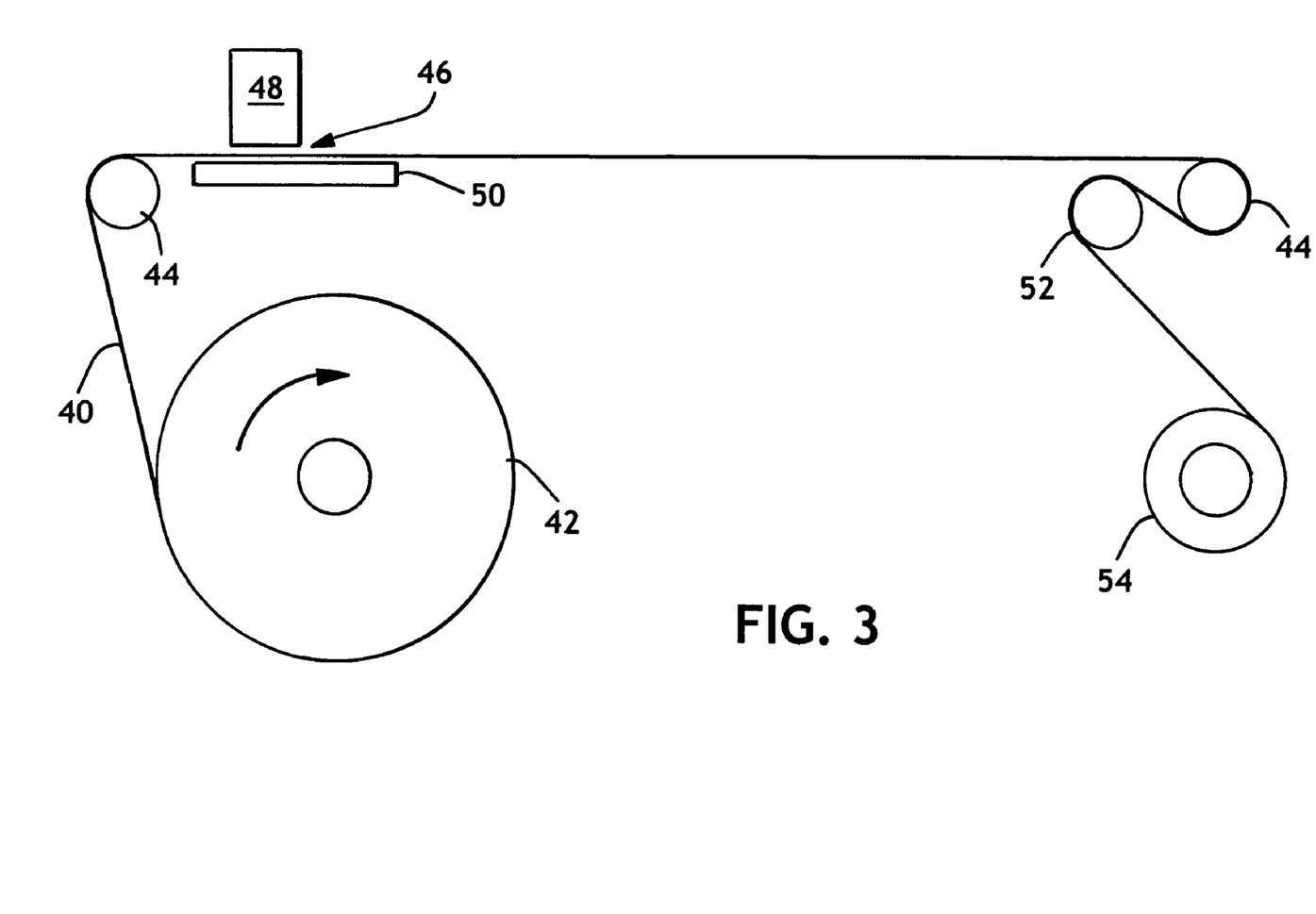
FIG. 3 is a schematic of an exemplary second step of a process of the invention using ink jet treating.

FIG. 3 shows schematically an exemplary second inline treatment step applied to web 40 having been previously treated as, for example, using the saturation spray device 12 of FIG. 1. In this embodiment, web 40 is unwound from roll 42 and directed around guide roll 44 through printing station 46 including ink jet printhead 48 and web support platen/exhaust hood 50. The web has applied to the surface facing the printhead a light application of the antistat. The web may then be directed by one or more drive rolls 52 and rewound into treated roll 54 or, optionally, otherwise processed.

Figure 4:
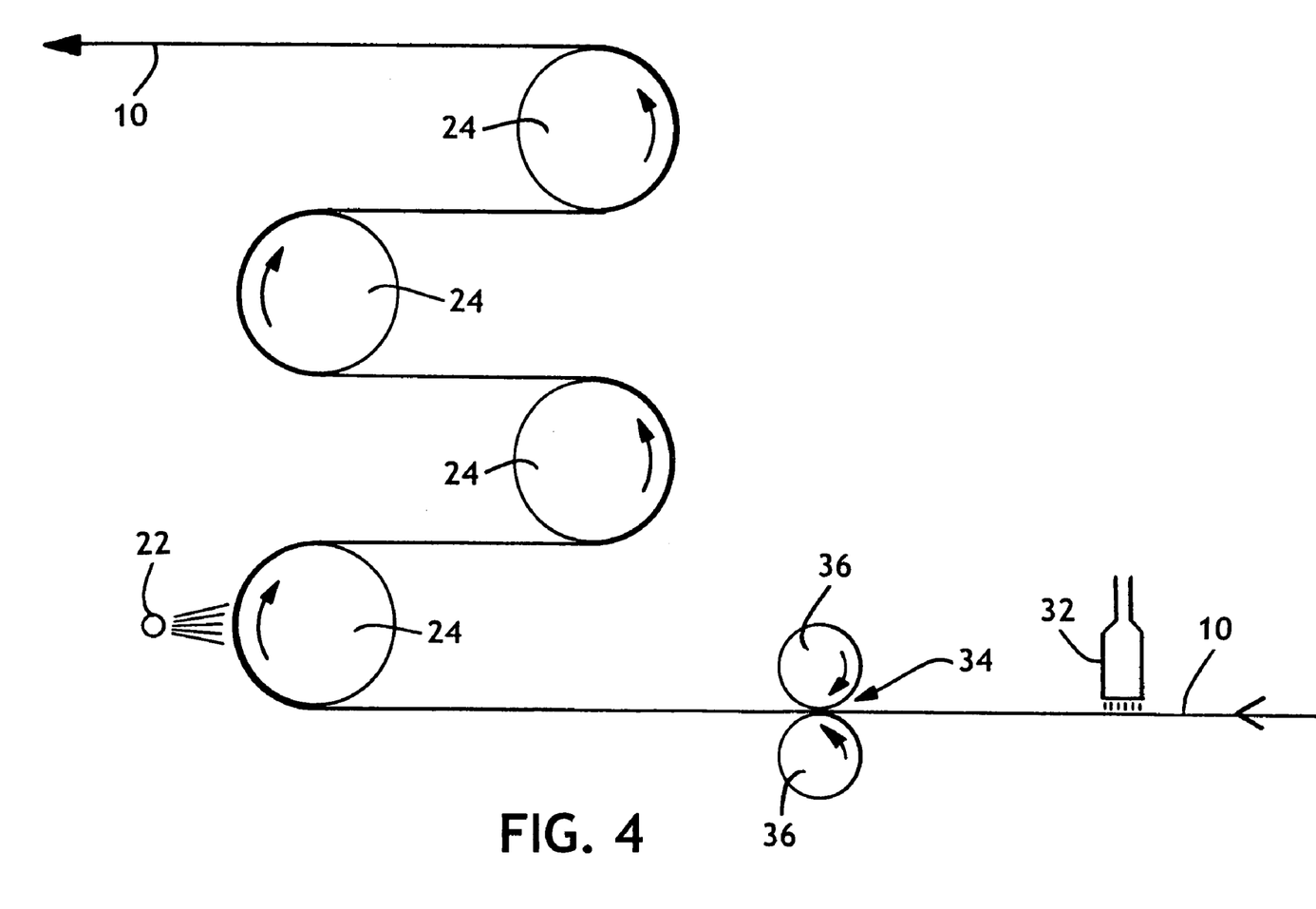
FIG. 4 is a schematic of a third treatment embodiment of the present invention applying antistat and repellent treatments to opposite sides.

FIG. 4 shows a third embodiment where the foam applicator 32 is used to apply fluorocarbon to one side of web 10 and spray 22 to apply antistat to the opposite side at steam can 24. Otherwise the process is like the process schematically illustrated in FIG. 2.

EXAMPLES

The present invention is further described by the examples which follow. Such examples, however, are not to be construed as limiting in any way either the spirit or the scope of the present invention.

For those examples using SMS fabric, the general process for forming the fabric and treating it was as follows:

A spunbond/meltblown/spunbond (SMS) laminate consisting of about 35 weight percent of a first spunbond layer, about 30 weight percent of meltblown layer and about 35 weight percent of a second spunbond layer was formed as described in U.S. Pat. No. 4,041,203 to Brock et al. After forming, the SMS laminate was thermally bonded with a bonding roll resulting in about 15 percent bond area in a wire weave pattern. The fabrics produced had a basis weight of about 1.5 oz/yd$^2$ (51 gsm) and about 1.2 osy (about 41 gsm) as specified in the respective example. After bonding, samples of the SMS laminates were treated offline using a batch process as described below. However, it is suggested that substrates may be treated inline by passing the substrate or a portion of the substrate through a saturator containing a bath as generally illustrated in FIG. 1. Each of the following examples was prepared in the same manner and samples of dried, treated material of each example were tested for alcohol repellency, water barrier as measured by hydrostatic head and fluorine add-on level to determine the add-on efficiency of the method.

The treatment compositions varied as specified in the each of the following Examples. A fluorine containing compound, for example an ionic fluoropolymer, was added to increase the isopropanol repellency of the finished, dried laminate. The amount of ionic fluoropolymer emulsion needed in the treatment composition is dependent upon the level of alcohol repellency desired and generally believed to be dependent of the specific ionic fluoropolymer chosen and the exposure time of the substrate to the treatment composition. In general, the less time that a laminate is exposed to a treatment composition, the greater the amount of ionic fluoropolymer emulsion is suggested in the bath to obtain the level of fluorine on the substrate to achieve a targeted level of repellency. For the Daikin UNIDYNE® TG-KC01 ionic fluoropolymer and process conditions chosen in the examples that follow, treatment compositions containing 0.4 weight percent, 0.55 weight percent and 0.69 weight percent of the ionic fluoropolymer were used. An alcohol, for example octanol, was added to aid in wetting out the laminate completely. As the water is dried off the laminate in a later step, the alcohol is volatilized. The amount of octanol used was typically 0.25 weight percent in the aqueous treatment bath.

The treatment solutions for each example were prepared as follows. Under vigorous mixing conditions, the specified weight of fluoropolymer emulsion was added to deionized water in a large mixing vessel. The specified amount of monovalent salt and antistatic agent, if any, and the specified amount of octanol was then added to the vessel and further mixed for an additional 2 minutes. The resulting emulsion was then fed into a saturation pan and continuously added to maintain the required amount of fluid necessary to saturate the SMS web passing through the equipment. The resulting wet pick up (WPU) of the formulation on the SMS was 300 percent by weight of the SMS. The WPU can be calculated as WPU=100%×(wet weight−dry weight)/dry weight. The SMS web then passed through a wringer capable of reducing the wet pick up from 300 percent down to 100 percent. The liquid that was removed from the sheet was allowed to recirculate back into the saturation pan. Finally, the treated SMS web passed through a large forced hot air drying unit capable of reducing the WPU from 100 percent to bone dry (0 percent WPU). The process described above was operated at 1000 feet per minute for the examples listed.

The percent fluorine add-on level on the samples was determined by an independent laboratory (Galbraith Laboratories of Knoxville, Tenn.) using an elemental analysis technique. The hydrostatic head of the samples was measured according to Federal Test Standard 191A, Method 5514. The alcohol repellency of the samples was measured by placing 0.1 ml of a specified percentage of isopropyl alcohol aqueous solution in several different locations on the surface of the fabric and leaving the specimen undisturbed for 5 minutes. The grading scale ranges from 0 to 5, with 0 indicating the IPA solution wets the fabric and 5 indicating maximum repellency. Unless stated otherwise, the percent alcohol (IPA) repellency reported indicates the maximum volume percent of IPA that could be added to water while still retaining a 5 rating on the scale at all points of the fabric tested. This procedure is a modification of INDA Standard Test No. IST 80.9-74 (R-82).

Comparative Example A

Comparative Example A consisted of untreated 1.5 osy SMS laminate fabric. The alcohol repellency of Comparative Example A was measured at 20 percent IPA. The water barrier property of Comparative Example A was measured at a hydrostatic head of 84.9±6.2 mBar. Only a trace amount of fluorine (less than 0.01 weight percent) was measured on Comparative Example A. The untreated 1.5 osy SMS fabric provided desirable water barrier but did not provide acceptable alcohol repellency.

Comparative Example B

Comparative Example B was a 1.5 osy SMS laminate treated in a bath that included an ionic fluoropolymer and an anionic antistatic agent. The aqueous treatment bath for Comparative Example B consisted of water in which was dissolved, or at least suspended, 0.69 weight percent of a cationic fluoropolymer suspension from Daikin America, Inc. identified as UNIDYNE® TG-KC01 and 0.30 weight percent of QUADRASTAT® PIBK anionic antistatic agent obtained from Manufacturers Chemical of Cleveland, Tenn. and 0.25 weight percent of octanol (a short chain alcohol that was used as a wetting agent) obtained from Aldrich Chemical. The alcohol repellency of Comparative Example B was measured at 90 percent IPA. The water barrier property of Comparative Example B was measured at a hydrostatic head of 46.3±3.1 mBar, which corresponds to a 45 percent drop in hydrostatic head compared to the untreated material. The fluorine loading on the dry SMS laminate of Comparative Example B was measured at 0.15 weight percent by Galbraith Laboratories of Knoxville, Tenn.

Example 1

Example 1 is an example of a method of treating a 1.5 osy nonwoven SMS fabric with a treatment solution that includes an ionic fluoropolymer, a monovalent salt and no antistatic agent. The treatment bath suspension of Example 1 consisted of a water bath in which was dissolved, or at least suspended, 0.69 weight percent of a cationic fluoropolymer suspension from Daikin America, Inc. and identified as UNIDYNE® TG-KC01, 0.30 weight percent of sodium nitrate ($NaNO_3$), a monovalent salt obtained from Aldrich Chemical, and 0.25 weight percent of octanol. For Example 1, the alcohol repellency was measured at 90 percent IPA, the water barrier property was measured at a hydrostatic head of 62.3±2.9 mBar, which corresponds to approximately a 30 percent drop in hydrostatic head compared to the untreated material. The fluorine loading on the dried SMS laminate of Example 1 was measured at 0.17 weight percent by Galbraith Laboratories of Knoxville, Tenn.

Example 2

Example 2 is another example of a method of treating a 1.5 osy nonwoven SMS nonwoven fabric With a treatment solution that includes an ionic fluoropolymer, a monovalent salt and no antistatic agent. The treatment bath suspension of Example 2 consisted of a water bath in which was dissolved, or at least suspended, 0.69 weight percent of a UNIDYNE® TG-KC01 cationic fluoropolymer suspension, 0.15 weight percent of sodium nitrate, and 0.25 weight percent of octanol. For Example 2, the alcohol repellency was measured at 90 percent IPA, the water barrier property was measured at a hydrostatic head of 66.0±3.5 mBar, which corresponds to approximately a 25 percent drop in hydrostatic head compared to the untreated material. The fluorine loading on the dried SMS laminate of Example 2 was measured at 0.19 weight percent.

Example 3

The treatment bath suspension for Example 3 consisted of a water bath in which was dissolved, or at least suspended, 0.40 weight percent of a UNIDYNE® TG-KC01 cationic fluoropolymer suspension, 0.15 weight percent of sodium nitrate, and 0.25 weight percent of octanol. For Example 3, the alcohol repellency was measured at 60 percent IPA, the water barrier property was measured at a hydrostatic head of 66.6±3.6 mBar, which corresponds to approximately a 25 percent drop in hydrostatic head compared to the Untreated material. The fluorine loading on the dried, 1.5 osy SMS laminate of Example 3 was measured at 0.10 weight percent.

Example 4

The treatment bath suspension for Example 4 consisted of a water bath in which was dissolved, or at least suspended, 0.69 weight percent of a UNIDYNE® TG-KC01 cationic fluoropolymer suspension, 0.075 weight percent of sodium nitrate, and 0.25 weight percent of octanol. For Example 4, the alcohol repellency was measured at 90 percent IPA, the water barrier property was measured at a hydrostatic head of 72.4±4.3 mBar, which corresponds to approximately a 15 percent drop in hydrostatic head compared to the Untreated material. The fluorine loading on the dried, 1.5 osy SMS laminate of Example 4 was measured at 0.19 weight percent.

Example 5

The treatment bath suspension for Example 5 consisted of a water bath in which was dissolved, or at least suspended, 0.55 weight percent of a UNIDYNE® TG-KC01 cationic fluoropolymer suspension, 0.075 weight percent of sodium nitrate, and 0.25 weight percent of octanol. For Example 5, the alcohol repellency was measured at 80% percent IPA, the water barrier property was measured at a hydrostatic head of 73.4±4.7 mBar, which corresponds to approximately a 15 percent drop in hydrostatic head compared to the untreated material. The fluorine loading on the dried, 1.5 osy SMS laminate of Example 5 was measured at 0.13 weight percent.

Example 6

The treatment bath suspension for Example 6 consisted of a water bath in which was dissolved, or at least suspended, 0.40 weight percent of a UNIDYNE® TG-KC01 cationic fluoropolymer suspension, 0.075 weight percent of sodium nitrate, and 0.25 weight percent of octanol. For Example 6, the alcohol repellency was measured at 60 percent IPA, the water barrier property was measured at a hydrostatic head of 71.4±4.5 mBar, Which corresponds to approximately a 15 percent drop in hydrostatic head compared to the untreated material. The fluorine loading on the dried, 1.5 osy SMS laminate of Example 6 was measured at 0.10 weight percent.

Example 7

The treatment bath suspension for Example 7 consisted of a water bath in which was dissolved, or at least suspended, 0.55 weight percent of a UNIDYNE® TG-KC01 cationic fluoropolymer suspension, 0.04 weight percent of sodium nitrate, and 0.25 weight percent of octanol. For Example 7, the alcohol repellency was measured at 80 percent IPA, the water barrier property was measured at a hydrostatic head of 78.9±4.6 mBar, which corresponds to less than a 10 percent drop in hydrostatic head compared to the untreated material. The fluorine loading on the dried, 1.5 osy SMS laminate of Example 7 was measured at 0.12 weight percent.

Although various embodiments of the invention have been described above using specific terms, devices, and methods, such description is for illustrative purposes only. The words used are words of description rather than of limitation. It is to be understood that changes and variations may be made by those of ordinary skill in the art without departing from the spirit or scope of the present invention, which is set forth in the following claims. In addition, it should be understood that aspects of the various embodiments may be interchanged both in whole or in part. Therefore, the spirit and scope of the appended claims should not be limited to the description of the preferred versions contained therein.

We claim:

1. A method of treating a substrate to improve the alcohol repellency of the substrate, the method comprising first passing a substrate through a first treatment solution comprising an ionic fluoropolymer and a monovalent salt wherein the first treatment solution does not include an organic phosphate ester or potassium isobutyl phosphate, and wherein the first treatment solution contains less than about 0.10 weight percent of the monovalent salt, and thereafter contacting the substrate with a second treatment solution comprising an antistatic agent selected from the group consisting of organic phosphate esters and mono- and di-substituted potassium isobutyl phosphates to form a treated substrate, wherein the treated substrate has a percent loss in hydrostatic head value as compared to untreated fabric of about 10% or less.

2. The method of claim 1, wherein the substrate is selected from the group consisting of nonwoven webs, foams, films, and porous films and the first treatment solution comprises less than about 0.005 weight percent by weight of an antistatic agent.

3. The method of claim 1, wherein the first treatment solution includes no antistatic agent.

4. The method of claim 1, wherein the substrate is a nonwoven fabric.

5. The method of claim 1, wherein the substrate is a nonwoven fabric laminate.

6. The method of claim 1, wherein the substrate is an infection control fabric that is or comprises a spunbond/meltblown/spunbond laminate, a spunbond/film/spunbond laminate, a spunbond/film/spunbond/meltblown/spunbond laminate or a spunbond/film/film/spunbond laminate.

7. The method of claim 1, wherein the first treatment solution comprises less than about 2 weight percent of an ionic fluoropolymer or a mixture of ionic fluoropolymers.

8. The method of claim 1, wherein the first treatment solution comprises less than about 1 weight percent of an ionic fluoropolymer or a mixture of ionic fluoropolymers.

9. The method of claim 1, wherein the first treatment solution comprises from about 0.1 weight percent to about 1 weight percent of an ionic fluoropolymer or a mixture of ionic fluoropolymers.

10. The method of claim 1, further comprising drying the treated substrate wherein the dried substrate comprises less than about 0.5 weight percent of fluorine.

11. The method of claim 1, further comprising drying the treated substrate wherein the dried substrate comprises less than about 0.25 weight percent of fluorine.

12. The method of claim 1, further comprising drying the treated substrate wherein the dried substrate comprises less than about 0.15 weight percent of fluorine.

13. The method of claim 1, wherein the first treatment solution is an aqueous treatment solution.

14. The method of claim 13, wherein the aqueous treatment solution further comprises an alcohol.

15. The method of claim 14, wherein the aqueous treatment solution comprises an alkyl alcohol.

16. The method of claim 1, wherein the ionic fluoropolymer is selected from the group consisting of fluoroalkyl acrylate homopolymers, fluoroalkyl acrylate copolymers, fluorinated siloxanes, fluorinated silicones, fluorinated urethanes, and mixtures thereof.

17. The method of claim 1, wherein the ionic fluoropolymer is a fluoroalkyl acrylate copolymer.

* * * * *